(12) United States Patent
Guarise et al.

(10) Patent No.: US 10,898,510 B2
(45) Date of Patent: Jan. 26, 2021

(54) SULPHATED HYALURONIC ACIDS FUNCTIONALISED WITH DOPAMINE

(71) Applicant: FIDIA FARMACEUTICI S.P.A., Abano Terme (PD) (IT)

(72) Inventors: Cristian Guarise, Abano Terme (IT); Stefano Pluda, Abano Terme (IT); Devis Galesso, Abano Terme (IT)

(73) Assignee: FIDIA FARMACEUTICI S. P. A., Abano Terme (IT)

( * ) Notice: Subject to any disclaimer, the term of this patent is extended or adjusted under 35 U.S.C. 154(b) by 0 days.

(21) Appl. No.: 16/344,449

(22) PCT Filed: Nov. 13, 2017

(86) PCT No.: PCT/IB2017/057070
§ 371 (c)(1),
(2) Date: Apr. 24, 2019

(87) PCT Pub. No.: WO2018/092013
PCT Pub. Date: May 24, 2018

(65) Prior Publication Data
US 2019/0321390 A1    Oct. 24, 2019

(30) Foreign Application Priority Data
Nov. 18, 2016 (IT) .................. 102016000117042

(51) Int. Cl.
| | | |
|---|---|---|
| *A61K 31/728* | (2006.01) | |
| *A61K 47/55* | (2017.01) | |
| *A61K 31/138* | (2006.01) | |
| *A61K 47/36* | (2006.01) | |
| *A61L 27/34* | (2006.01) | |
| *A61L 27/54* | (2006.01) | |

(52) U.S. Cl.
CPC .......... *A61K 31/728* (2013.01); *A61K 31/138* (2013.01); *A61K 47/36* (2013.01); *A61K 47/55* (2017.08); *A61L 27/34* (2013.01); *A61L 27/54* (2013.01)

(58) Field of Classification Search
CPC ..... A61K 31/728; A61K 47/55; A61K 31/138
See application file for complete search history.

(56) References Cited

U.S. PATENT DOCUMENTS 7,928,069 B2 * 4/2011 Prestwich ............ C07K 1/1072
514/17.2

FOREIGN PATENT DOCUMENTS

WO    WO 2010/130468 A1    11/2010

OTHER PUBLICATIONS

International Search Report, issued in PCT/IB2017/057070, dated Apr. 1, 2018.
Lee et al., "Thermo-sensitive, injectable, and tissue adhesive sol-gel transition hyaluronic acid/pluronic composite hydrogels prepared from bio-inspired catechol-thiol reaction", Soft Matter, 2010, vol. 6, pp. 977-983, XP055376863.
Magnani et al., "Hyaluronic acid and sulfated hyaluronic acid in aqueous solution: effect of the sulfation on the protonation and complex formation with $Cu^{2+}$ and $Zn^{2+}$ ions", Macromol. Chem. Phys., 1999, vol. 200, pp. 2003-2014, XP000866771.
Neto et al., "Nanostructured Polymeric Coatings Based on Chitosan and Dopamine-Modified Hyaluronic Acid for Biomedical Applications", small, 2014, vol. 10, No. 12, pp. 2459-2469, XP055376688.
Satoh et al., "The basic research on physiological property of functionalized hyaluronan-l. Effect of hyaluronan and sulfated hyaluronan on cell proliferation of human epidermal keratinocytes", Polym. Adv. Technol., 2004, vol. 15, pp. 329-334, XP001226876.
Written Opinion of the International Searching Authority, issued in PCT/IB2017/057070, dated Apr. 1, 2018.

* cited by examiner

*Primary Examiner* — Pancham Bakshi
(74) *Attorney, Agent, or Firm* — Birch, Stewart, Kolasch & Birch, LLP

(57) ABSTRACT

Disclosed is grade 2 sulphated hyaluronic acid having 2 to 60% molar, preferably 15 to 35%, and even more preferably between 20 and 25%, of the carboxyl groups functionalized with dopamine conjugated directly via an amide bond or by means of a spacer having an amino group for the formation of an amide bond with the carboxyl groups of hyaluronic acid and of a carboxyl group for the formation of an amide bond with the amino group of dopamine.

20 Claims, 7 Drawing Sheets

SULPHATED HYALURONIC ACIDS FUNCTIONALISED WITH DOPAMINE

The invention relates to sulphated hyaluronic acids functionalized with dopamine by means of amide bonds, which may be direct or via a suitable spacer group. The compounds of the invention form salts with medicaments having ionizable groups with positive charges, in particular antibiotics. A further object of the invention is said salts and their use to coat titanium endoprostheses implantable in living organisms or biomedical devices in general.

PRIOR ART

Hyaluronic acid (HA) is a heteropolysaccharide consisting of alternating residues of D-glucuronic acid and N-acetyl-D-glucosamine, with a straight chain, having a molecular weight ranging between 50000 and $13 \times 10^6$ Da, depending on the source from which it is obtained and the preparation methods used.

Hyaluronic acid is practically ubiquitous in the human body, in which it plays an important role, especially as mechanical support for the cells of many tissues, such as skin, tendons, muscles and cartilage. The interactions of HA with its CD44 membrane receptor and opioid receptors are also known.

O-sulphated HA derivatives, wherein the —OH groups are esterified with sulphuric acid, are known. O-sulphation can be performed by known techniques (see, for example, EP702699 and EP940410); "degree of sulphation" means the moles of sulphate groups per mole of HA dimer (DS-mol); specifically:

grade 1 sulphation defines a DSmol ranging between 0.5 and 1.5;

grade 2 sulphation defines a DSmol ranging between 1.5 and 2.5;

grade 3 sulphation defines a DSmol ranging between 2.5 and 3.5.

In general, HAS crosses the skin barrier easily, thus simplifying the passage of substances associated with it, and is therefore an excellent carrier for cutaneous absorption of pharmacologically and biologically active molecules.

It has also been discovered (WO2010130468; WO2010130466) that HAS possesses pharmacological properties: it is a potent anti-inflammatory, which performs its action by means of effective modulation of the activities of numerous pro- and anti-inflammatory cytokines. HAS is therefore suitable for use in the treatment of disorders mediated by alteration of the cytokine levels (rheumatoid arthritis, asthma, systemic and cutaneous autoimmune diseases, viral infections, atopic dermatitis, eczema, vitiligo, lymphomas, etc.).

DOPA (1-3,4-dihydroxyphenylalanine), an amino acid intermediate in dopamine synthesis, is a known neurotransmitter, and was recently also studied as an adhesive substance. A significant concentration of DOPA residues has been found in the amino acid composition of the proteins called "*Mytilus edulis* foot proteins" (Mefp, in particular Mefp-3 and Mefp-5), which constitute the peduncle with which *Mytilus edulis*, commonly known as the mussel, adheres to surfaces. The key characteristic of DOPA is the catechol group; this suggests that a high concentration of catechol units plays a key role in promoting adhesion to multiple surfaces, including glass, plastic, ceramic, and surfaces based on metals and metal oxides. Although the mechanism whereby said adhesion takes place is not yet fully understood, adhesion is known to take place in both an acid medium (pH=5) and an alkaline medium (pH=8), when the catechol groups take the form of quinones. As the dopamine derivative also possesses identical characteristics, DOPA and dopamine are indiscriminately defined and used in the scientific literature in terms of adhesive activity.

HA, both "as is" and in its sulphated form, has been used, combined with other polymers, in the coating of metal (usually titanium) and polymer (e.g. PU) prostheses to promote bio- and haemocompatibility (EP1060204).

DOPA has also already been used as adhesive to promote the bond with other molecules (usually polymers) having a metal core (Lee et al., Adv Mat, 2008, 20, 4154-4157).

Finally, there are examples wherein a metal prosthesis is coated with DOPA conjugated with a polymer which, in turn, can bond to an antibiotic, thereby reducing the probability of bacterial proliferation. For example, Lee et al. (Bone, 2012, 50, 974-982) describe DOPA conjugated with heparin and further functionalized with an antibiotic and BMP2, to promote the osseointegration of titanium dental prostheses. Heparin is selected because it contains sulphate groups that render the conjugate globally negatively charged, and therefore able to bond to the positively-charged antibiotic. However, the presence of heparin is critical, because its well-known anticoagulant activity can be problematic and create abnormal bleeding during and after implantation.

DESCRIPTION OF THE INVENTION

It has now been found that conjugates of sulphated hyaluronic acid (HAS) and dopamine can be advantageously used to adsorb a positively-charged biologically and/or pharmacologically active antibiotic or molecule by means of electrostatic interaction. Conjugates of HAS and dopamine functionalized with medicaments or other active compounds are useful for coating biomedical articles in general and titanium prosthesis in particular, to make them biocompatible and, especially in the case of titanium prosthesis, to improve their integration with the bone matrix onto which they are grafted. The conjugates of sulphated hyaluronic acid (HAS) and dopamine described herein have proved particularly effective when used with either classic titanium prostheses, which have a compact structure, or with the latest-generation prostheses, which have a porous (trabecular) crosslinked structure, perfectly integratable with the bone. After implantation, the trabecular prosthesis treated with the conjugates described herein is not only biocompatible but, due to its specific structure, is also colonized by the cells and integrates perfectly with the bone.

The conjugates of sulphated hyaluronic acid (HAS) and dopamine forming the object of the invention also play a leading part in reducing the possible infections deriving from the implant. This latter aspect is particularly important because bacterial growth and subsequent biofilm formation represents a major complication, not so much at the stage of primary implantation of an artificial knee, hip, etc., as after the first review of the prosthesis, leading to the need for removal in 5-40% of cases. It is estimated that about 80% of infections leading to prosthesis removal are due to formation of a bacterial biofilm.

The biofilm is an accumulation of micro-organisms (*Staphylococcus aureus, S. epidermidis, S. haemolyticus,* etc.) with high bacterial density, encapsulated in a polysaccharide matrix and adhering to a solid biological or nonbiological surface, usually resistant to systemic treatment with antibiotics.

The sulphated hyaluronic acid used according to the invention is grade 2 (HAS2), namely a HAS wherein the moles of the sulphate groups per mole of HA dimer (DSmol) range between 1.5 and 2.5.

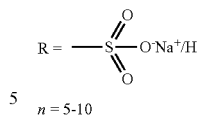

$n = 5$-$10$

Scheme C

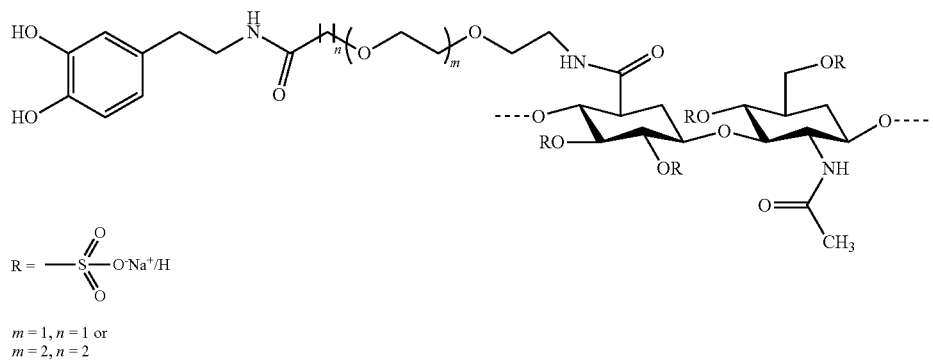

$m = 1, n = 1$ or
$m = 2, n = 2$

The percentage functionalisation of the carboxyl groups of HAS2 with dopamine, bonded directly or via a spacer, ranges between 2 and 60% molar for both the direct and the indirect bond; it preferably ranges between 15 and 40%, and even more preferably between 20 and 32%, for the direct bond, whereas for the indirect bond it preferably ranges between 2 and 20%.

The bond between dopamine and HAS2 is the amide type, and may be direct (COOH of HA-NH$_2$ of dopamine) as shown in Scheme A, or indirect, when a spacer is inserted between dopamine and HAS, always bonded via an amide bond, to maximize the interaction of the dopamine with the titanium surface to be functionalized, thereby reducing the steric effect of HAS2. The spacer used can be an alkyl chain with a length ranging between 5 and 10 methylene units, preferably 5 or 10 (Scheme B), or a polyethylene glycol chain of formula HOOC—(CH$_2$)$_n$—O—[(CH$_2$)$_n$—O]$_m$—(CH$_2$)$_2$—NH$_2$ (Scheme C).

Scheme A

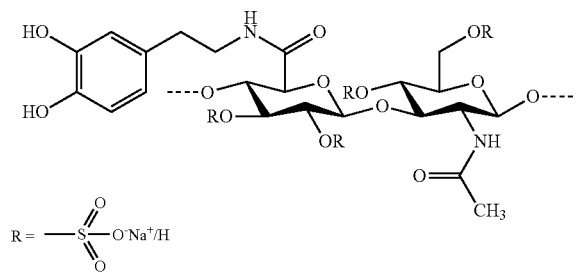

Scheme B

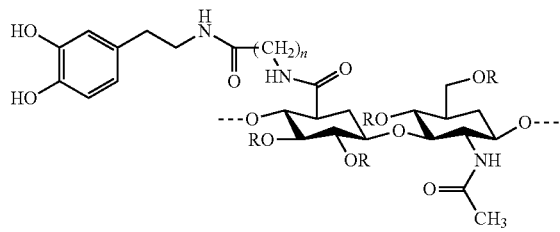

The spacer therefore has an amino group for the formation of an amide bond with the carboxyl groups of hyaluronic acid, and a carboxyl group for the formation of an amide bond with the amino group of dopamine.

Spacer compounds suitable for use in the preparation of the grade 2 sulphated hyaluronic acids of the invention have the following formulas:

HOOC—(CH$_2$)$_n$—NH$_2$ wherein n is an integer from 5 to 10, and is preferably 5 or 10;

HOOC—CH$_2$—(O—CH$_2$—CH$_2$)$_m$—O—CH$_2$—CH$_2$—NH$_2$ wherein m is 1 or 2.

Said compounds are known or can be prepared by known methods.

The reaction between HAS2 and dopamine takes place using known conditions for the formation of amide bonds, for example in the presence of condensing agents such as carbonyldiimidazole (CDI) or diimides.

For the preparation of derivatives wherein dopamine is bonded via a spacer to sulphated hyaluronic acid, it is preferable to synthesize the dopamine-spacer intermediate first and then conjugate the intermediate with HAS2. The spacer, suitably protected at the amino group, can be reacted with dopamine hydrochloride in the presence of conventional condensing agents and bases. The resulting intermediate, after removal of the protecting group, is then reacted with HAS2 under the conditions described above for the formation of amide bonds.

The starting hyaluronic acid can derive from any known source, for example by extraction from rooster combs (EP138572), fermentation or biosynthesis (from *Bacillus*, WO2012032154); in this specific case grade 2 HAS is used, prepared from HA with a weight average MW ranging between 100,000 and 250,000 Da, in particular between 180,000 and 230,000 Da, hereinafter called "MW 200 kDa". The preparation is conducted by known methods (EP0702699; IT102015000073016), and is reported in the examples.

"Average molecular weight" (MW) here means the weight-average MW, calculated by the "intrinsic viscosity" method (Terbojevich et al., Carbohydr. Res., 1986, 363-377).

The compounds of the invention can be used as drug carriers and for coating endoprostheses.

Implantable prostheses, mainly made of titanium-based metal, with a compact or trabecular structure, are coated simply by spraying a solution of the compounds of the invention onto the prosthesis, optionally followed by spraying a solution of antibiotics or biologically or pharmacologically active substances, suitably treated so as to have a positive charge, such as growth factors (BMP-2; TGF1β; IGF) or synthetic molecules, already known for their inhibiting effect on biofilm formation (such as diclofenac in acid form).

The usable antibiotics are those which are positively chargeable, in particular Gentamicin, Daptomycin, Vancomycin, Ciprofloxacin, Meropenem, Amikacin, Tobramycin, Polymyxin, Colistin and Bacitracin, preferably Gentamicin, Colistin and Daptomycin.

Said antibiotics form salts with grade 2 sulphated hyaluronic acids functionalized with dopamine. Said salts and the prostheses on which they are adsorbed are a further object of the invention.

The HAS2-dopamine compound of the invention has the following advantages over the prior art:
- it is sprayable. While the prior art requires the prosthesis to be immersed, sometimes for long periods (hours), in the solution containing the "adhesive" polymer, the present invention is applied by simple spraying, even directly in the operating theatre, ensuring even, homogeneous coverage, total maintenance of sterility, and above all a significant reduction, or even elimination, of adhesion and drying times prior to implantation of the prosthesis;
- it adheres perfectly to the metal prosthesis;
- it is biocompatible;
- it retains the surface roughness of the prosthesis, required to promote integration with the bone matrix;
- it is sterilizable by the best-known techniques (irradiation with beta or gamma rays) and, after sterilization, maintains its structural characteristics intact (no oxidative degradation of dopamine) and therefore, after conjugation with an antibiotic, also maintains its biological efficacy (unchanged antibacterial activity). This means that, when necessary, the prosthesis to be implanted can be coated with HAS2-DOPA, sterilized, stored long before use in the operating theatre, and sprayed with antibiotic at the time of use, in which case there is no need to wait until the end of prosthesis adhesion and drying times in the operating theatre, which is particularly important in the case of long operations;
- it stimulates osteoblast regeneration;
- it creates a set of negative charges suitable for electrostatic interaction with positively-charged antibiotics (or active molecules in general). In this way the onset of infections is considerably reduced, because the formation of a bacterial biofilm is prevented or strongly limited;
- it has practically no heparin-like effect, although it contains sulphate groups, and therefore does not give rise to abnormal bleeding,
- it acts in an exceptionally effective, rapid, lasting way.

PREPARATION EXAMPLES

Figure 1:
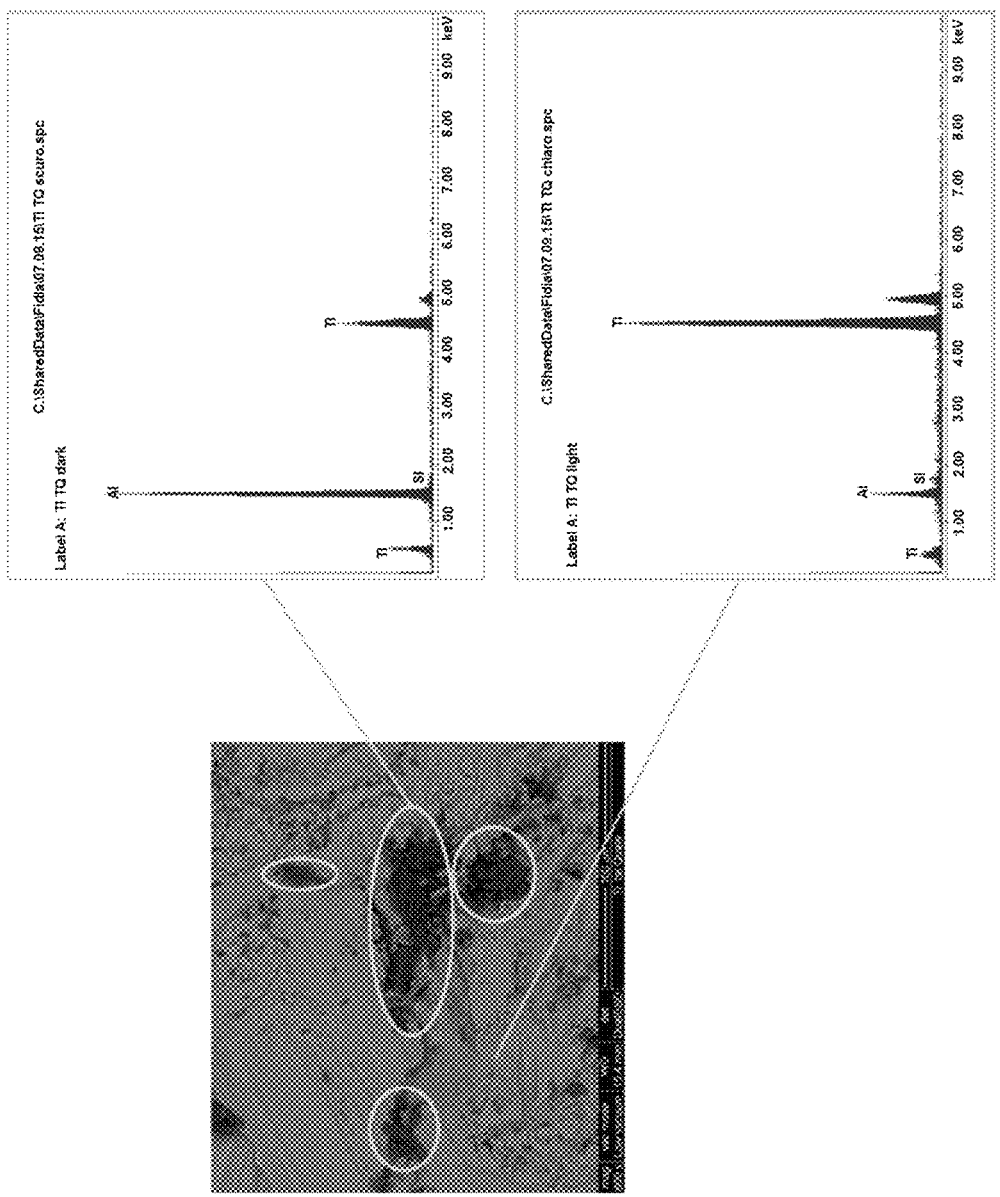
FIG. 1: ESEM image of the surface of an untreated titanium cylinder and the corresponding XPS spectra of the highlighted zones.

Conjugates of grade 2 sulphated hyaluronic acid with dopamine (hereinafter called HAS2-DOPA) are synthesized in two steps: synthesis of HAS2 and the reaction between HAS2 and dopamine. HAS2, in turn, can be prepared from HA salified with tetrabutylammonium (TBA; EP702699) or salified with sodium (IT102015000073016).

Example 1: Preparation of HAS2 from HA-TBA 2.0 g d.m. ($3.22 \times 10^{-3}$ mol; 1 eq) of HA$^-$ TBA$^+$ (MW 200 kDa) was dissolved in 200 mL of DMSO. When dissolution was complete, 3.59 g of Pyr.SO3 (8 eq) was added. After being left overnight at room temperature the product was precipitated with EtOH, and the precipitate obtained was filtered, washed twice with EtOH and redissolved in 150 mL of deionized water: 8 mL of saturated solution of NaCl and 115 mL of DMSO were added, and the pH was corrected to 3.4±0.1 with 3M NaOH. The product was precipitated with 440 mL of EtOH, and the precipitate obtained was filtered, washed with EtOH/H$_2$O mixture (80:20) and with EtOH, and finally dried under vacuum at 37° C.

Example 2: Preparation of HAS2 from HA-Na 4.0 g d.m. ($9.96 \times 10^{-3}$ mol; 1 eq) of HA$^-$ Na (MW 200 kDa) was dispersed in 220 mL of DMSO; 3.6 mL of methanesulphonic acid (5 eq) was added, and the mixture was left under stirring for 24 h at room temperature. When dissolution was complete, 12.8 g of Pyr.SO$_3$ (8 eq) was added. After being left overnight at room temperature the product was precipitated with EtOH, and the precipitate obtained was filtered in a Gooch, washed twice with EtOH and redissolved in 150 mL of deionized water; 8 mL of saturated solution of NaCl and 115 mL of DMSO were added, and the pH was corrected to 3.4±0.1 with 3M NaOH. The product was precipitated with 440 mL of EtOH, and the precipitate obtained was filtered, washed with EtOH/H$_2$O mixture (80:20) and with EtOH, and finally dried under vacuum at 37° C.

Example 3: Synthesis of HAS2-DOPA Conjugate with 23% Derivatization (Direct Bond)

2.0 g d.m. ($3.3 \times 10^{-3}$ mol, 1 eq) of HAS2 sodium salt prepared as in Example 2 was dissolved in 100 mL of deionized water, and 3.0 g of benzalkonium chloride (BA$^+$ Cl⁻) was dissolved separately in 100 mL of deionized water. When solubilization was complete the BA⁺Cl⁻ solution was added to the HAS2 solution, thus obtaining a precipitate, which was filtered, washed in $H_2O$, in EtOH and then in acetone, and dried in a rotary evaporator under high vacuum. The precipitate isolated was solubilized in 160 mL of DMSO; 0.267 g (0.5 eq) of CDI and 0.1 mL of methanesulphonic acid (0.5 eq) were then added. After 30 min. stirring at 40° C., 0.5 g (0.8 eq) of dopamine hydrochloride was added, and the reaction continued overnight under slow stirring at 40° C. 16 mL of saturated NaCl solution was added the next day, and the product was precipitated with EtOH. The precipitate obtained was filtered and washed with 2 volumes of a mixture consisting of EtOH/$H_2O$ (85:15), then with EtOH, and finally with acetone. The resulting product was dissolved in 50 mL of deionized $H_2O$ and dialyzed (Spectra/Por® dialysis membrane with cut-off=12,000-14,000 Da) for 3 days in 0.05 M acetate buffer pH 5, and for 1 day in $H_2O$ adjusted to pH 5 by adding 1 M HCl.

The dialysis time was regulated, verifying the disappearance of free dopamine in the dialysis membrane by GPC. Finally, the dialyzed product was frozen and freeze-dried.

Example 4: Synthesis of HAS2-DOPA Conjugate with 55% Derivatization (Direct Bond)

The derivative was synthesized and characterised as described in Example 3, starting with 2 g of HAS2 sodium salt, salified with BA and reacted with 1.34 g (2.5 eq) of CDI and 2.5 g (4.0 eq) of dopamine hydrochloride.

Example 5: Synthesis of HAS2-DOPA Conjugate with 31% Derivatization (Direct Bond)

The derivative was synthesized and characterised as described in Example 3, starting with 2 g of HAS2 sodium salt, salified with BA and reacted with 0.801 g (1.5 eq) of CDI and 1.25 g (2.0 eq) of dopamine hydrochloride.

Example 6: Synthesis of HAS2-DOPA Conjugate with 21% Derivatization (Direct Bond)

The derivative was synthesized and characterised as described in Example 3, starting with 2 g of HAS2 sodium salt, salified with BA and reacted with 0.134 g (0.25 eq) of CDI and 0.25 g (0.4 eq) of dopamine hydrochloride.

Example 7: Synthesis of HAS2-DOPA Conjugate with 6% Derivatization (Direct Bond)

The derivative was synthesized and characterised as described in Example 3, starting with 2 g of HAS2 sodium salt, salified with BA and reacted with 0.067 g (0.125 eq) of CDI and 0.25 g (0.4 eq) of dopamine hydrochloride.

Example 8: Synthesis of HAS2-CONH—$(CH_2)_{10}$—CONH-Dopamine Conjugate with 5% Derivatization (Indirect Bond Via Alkyl Spacer with 10 Carbon Atoms)

The indirect bond involves two steps: synthesis of the dopamine-spacer species followed by synthesis of dopamine-spacer with HAS2:

8.1: Dopamine-Spacer Synthesis: $NH_2$—$(CH_2)_{10}$—CONH-Dopamine 0.55 g of 11-(Boc-amino)undecanoic acid was dissolved in 10 mL of DMF, and the carboxyl was activated with 0.56 g of EDC (N-ethyl-N'-(3-dimethylaminopropyl)carbodiimide hydrochloride), adding DMAP (0.07 g) in the presence of a tertiary base (TEA, 0.31 mL) at 0° C. under stirring. 0.4 g of dopamine hydrochloride was added after 10 min., and the mixture was left under stirring at RT overnight. 40 mL of dichloromethane and 40 mL of $H_2O$ were then added, and the organic phase was extracted, washed in water and dried in a rotovap. The BOC protecting group was released by adding 5 mL of the following acid mixture: TFA 15%/$H_2O$ 5%/DCM 80%, and leaving the resulting mixture under stirring for 20 min at RT. The solvent was then evaporated and the product was dried.

8.2: Synthesis of HAS2-CONH—$(CH_2)_{10}$—CONH-DOPA

The derivative was synthesized and characterised as described in Example 3, starting with 1 g of HAS2 sodium salt, salified with BA and reacted with 0.45 g of CDI and 0.5 g of $NH_2$—$(CH_2)_{10}$—CONH-DOPA obtained as in Example 8.1.

Example 9: Synthesis of HAS2-CONH—$(CH_2)_5$—CONH-Dopamine Conjugate with 5% Derivatization (Indirect Bond Via Alkyl Spacer with 5 Carbon Atoms)

The dopamine-spacer was obtained by using 6-(Boc-amino)caproic acid as reagent and following the procedure described in example 8.1.

The product HAS2-CONH—$(CH_2)_5$—CONH-dopamine was obtained according to the procedure described in example 8.2.

Example 10: Synthesis of HAS2-CONH—$(CH_2)_2$—O—$(CH_2)_2$—O—$CH_2$—CONH-DOPA Conjugate with 5% Derivatization (Indirect Bond Via Polyethylene Glycol Spacer)

The indirect bond involves two steps: synthesis of the DOPA-spacer species followed by synthesis of DOPA-spacer with HAS2.

DOPA-Spacer Synthesis: $NH_2$—$(CH_2)_2$—O—$(CH_2)_2$—O—$CH_2$—CONH-DOPA 0.64 g of Boc-NH—(PEG)-COOH. DCHA (9 atoms) was dissolved in 10 mL of DMF and the carboxyl was activated with 0.56 g of EDC (N-ethyl-N'-(3-dimethylaminopropyl)carbodiimide hydrochloride), adding DMAP (0.07 g) in the presence of a tertiary base (TEA, 0.31 mL) at 0° C. under stirring. After 10 min the DOPA (dopamine hydrochloride) was added and left under stirring at RT overnight. 40 mL of dichloromethane and 40 mL of $H_2O$ were then added, and the organic phase was extracted, washed in water and dried in a rotary evaporator. The BOC protecting group was released by adding 5 mL of the following acid mixture: TFA 15%/$H_2O$ 5%/DCM 80%, and leaving under stirring for 20 min at RT. The solvent was then evaporated and the product was dried. 0.5 g of product was obtained (83% yield).

Synthesis of HAS2-CONH—$(CH_2)_2$—O—$(CH_2)_2$—O—$CH_2$—CONH-DOPA

The derivative was synthesized as previously described for the HAS2-DOPA derivative, starting with 1 g of HAS2 sodium salt, salified with BA and reacted with 0.45 g of CDI and 0.5 g of $NH_2$—$(CH_2)_2$—O—$(CH_2)_2$—O—$CH_2$—CONH-DOPA.

Example 11 (Comparative): Synthesis of Heparin (HEPA)-DOPA Conjugate with 21% Derivatization (Prepared According to Lee et al., 2012)

1.0 g d.m. ($3.3 \times 10^{-3}$ mol, 1 eq) of heparin sodium (HEPA) was dissolved in 50 mL of deionized water, and 1.5 g of benzalkonium chloride (BA$^+$Cl$^-$) was dissolved separately in 100 mL of deionized water. When solubilization was complete the BA$^+$Cl$^-$ solution was added to the HEPA solution, thus obtaining a precipitate which was filtered, washed in H$_2$O, in EtOH and then in acetone, and dried in a rotary evaporator under high vacuum. The precipitate isolated was solubilized in 80 mL of DMSO; 0.134 g (0.5 eq) of CDI and 0.05 mL of methanesulphonic acid (0.5 eq) were then added. After 30 min. stirring at 40° C., 0.25 g (0.8 eq) of dopamine hydrochloride was added, and the reaction continued overnight under slow stirring at 40° C. 8 mL of saturated NaCl solution was added the next day, and the product was precipitated with EtOH. The ppt obtained was filtered and washed with 2 volumes of a mixture consisting of EtOH/H$_2$O (85:15), then with EtOH, and finally with acetone. The resulting product was dissolved in 50 mL of deionized H$_2$O and dialyzed (Spectra/Por® dialysis membrane with cut-off=3,000 Da) for 3 days in 0.05 M acetate buffer pH 5 and 1 day in H$_2$O adjusted to pH 5 by adding 1 M HCl.

The dialysis time was regulated, verifying the disappearance of free dopamine in the dialysis membrane by GPC.

Example 12 (Comparative): Synthesis of HA-DOPA Conjugate with 23% Derivatization The HA-DOPA derivative was synthesized by the procedure described in Example 3, starting with 1.32 g (0.0033 moles) of HA sodium salt 200 kDa, salified with BA and reacted with 0.267 g (0.5 eq) of CDI and 0.5 g (0.8 eq) of dopamine hydrochloride.

Example 13: Test of Adhesion of HAS2-DOPA Derivative

As dopamine acts as an adhesive at various pH values, its ability to coat the HAS2-DOPA conjugate (prepared as described in Example 5), dissolved in PBS at the two most representative pH values, namely 5 and 8, was tested:
Solution A: 20 mg of HAS2-DOPA (31%) in 4 mL of 0.1 M MES pH 5.
Solution B: 20 mg of HAS2-DOPA (31%) in 4 mL of 0.1 M PBS pH 8.
A fluorescent probe positively charged at any pH (Sanguinarine hydrochloride) was used for this test, to simulate the interaction of the derivative with a positively-charged antibiotic at physiological pH.

Two titanium cylinders (d=15×h=17 mm) were evenly sprayed with solution A and solution B respectively, washed with deionized water, dried in an airflow and immersed in different vials containing a Sanguinarine solution at the concentration of 0.5 mg/mL in 0.1 M MES, pH 5. The cylinders were left under gentle stirring overnight at RT. The next day the cylinders were washed again with deionized water, dried under N$_2$ flow and irradiated with a UV lamp at 360 nm, conducting a visual inspection.

From the evaluation of the fluorescence emitted by the treated cylinders it was deduced that the dopamine derivative at pH 8 (Solution B) adhered best to the surface. This finding demonstrates that solution B represents the ideal approach for the purpose of embodying the present invention.

13.1: Electron Microscope (ESEM) Analysis of Titanium Surface Coating

Figure 2:
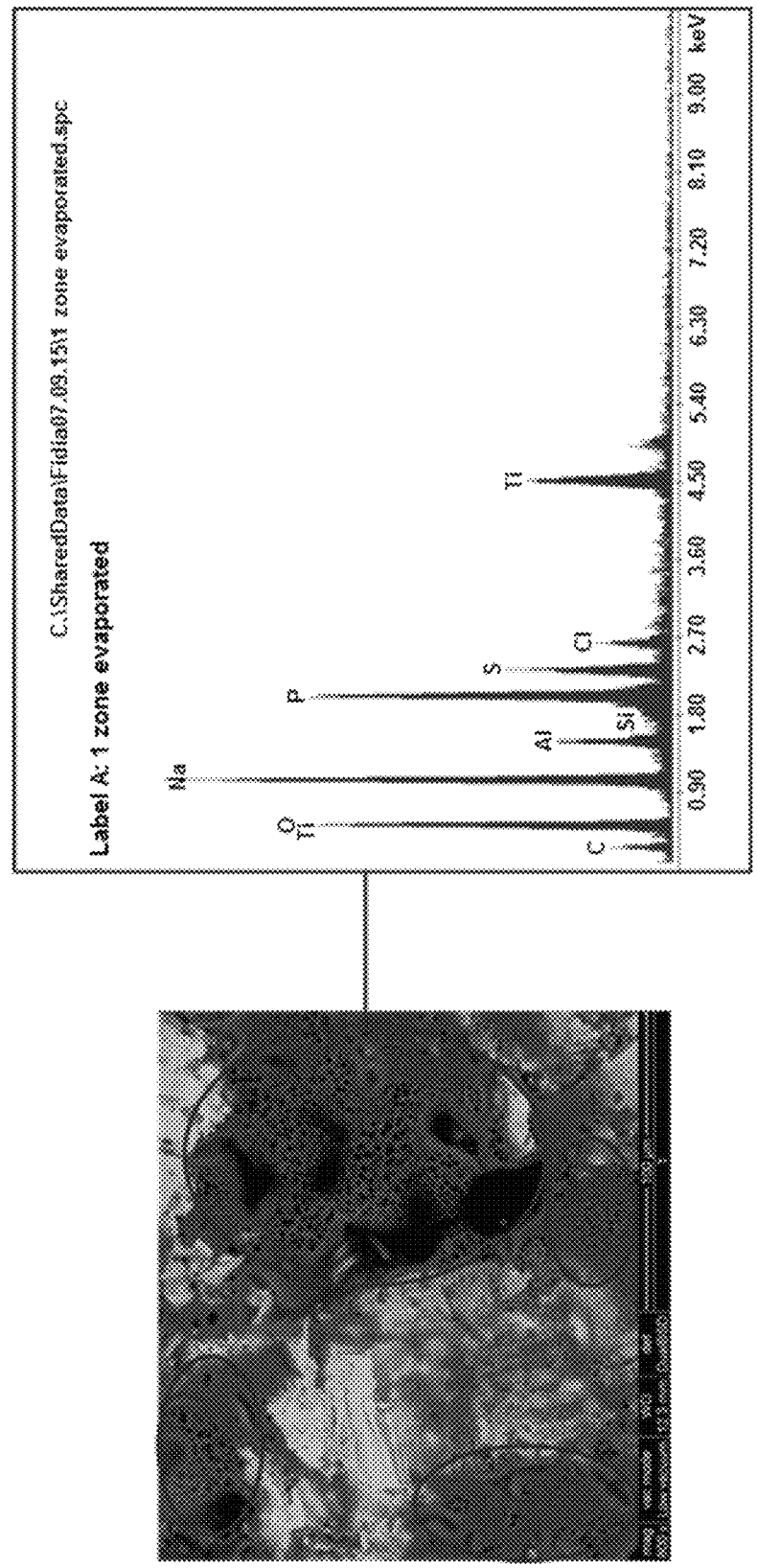
FIG. 2: ESEM image of the surface of a titanium cylinder coated with the derivative of example 3 and the corresponding XPS spectra of the highlighted zones.
Figure 3:
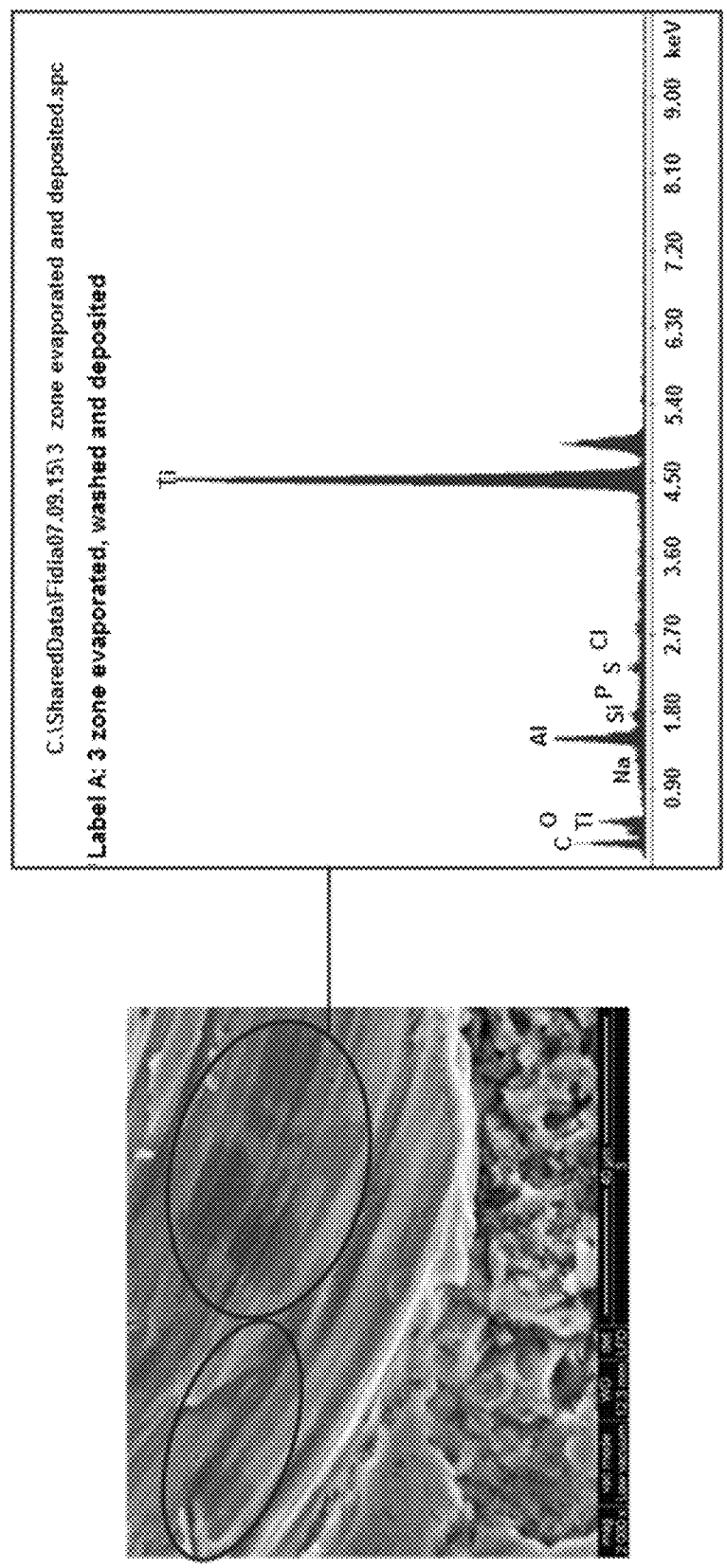
FIG. 3: ESEM image of the surface of the cylinder treated with the derivative of example 3 and then washed.

This test established that the HAS2-DOPA derivative deposited by spraying on the surface of the cylinder not only adheres evenly to Ti, but maintains the surface roughness needed to promote osteointegration of the prosthesis with the bone matrix. A solution of HAS2-DOPA (23%; Example 3) 25 mg/mL in 0.1 M PBS, pH 8, was prepared, and 1 ml of said solution was sprayed onto a Ti cylinder; it was left to air-dry and the surface was observed under an ESEM, comparing it with that of an untreated cylinder (FIGS. 1 and 2). Qualitative XPS analysis (photoelectron X-ray spectroscopy, which detects the presence of organic material on the surface analysed) was conducted in addition to photographic scanning. The treated cylinder was then washed to establish whether the derivative continued to adhere to the surface even in a situation where, as after implantation in vivo, it is in contact with a flow of physiological fluids (FIG. 3).

The image of the treated surface clearly shows the presence of material, confirmed by the XPS analysis. Moreover, the dried derivative creates surface irregularities that give the surface a rough texture, which is an important parameter in promoting integration of the implant with the bone matrix.

After washing, derivative residues were still visible on the surface, confirming that the derivative interacts actively with Ti, and continues to adhere even after washing.

This demonstrates that the HAS2-DOPA conjugate:
adheres perfectly to the titanium surface, especially when prepared in solution at pH=8;
it also remains bonded to the surface after washing;
and gives the metal surface the rough texture needed to promote osteointegration of the prosthesis.

Example 14: In Vitro Test of Inhibition of *S. aureus* Bacterial Growth (Titanium Cylinder Functionalized with HAS2-DOPA or HA-DOPA and Gentamicin)

The following were prepared:
a solution of HAS2-DOPA (23%, Example 3) in 0.1 M PBS, pH=8;
a solution of HA-DOPA (23%, Example 12) in 0.1 M PBS, pH=8;
a Gentamicin solution (25 mg/5 ml of 0.25 M MES, pH=5.2);
a solution of 0.1 M PBS, pH=8 (control).
2 titanium cylinders (d=15×h=17 mm) were sprayed with the HAS2-DOPA solution, left to air-dry for 15 minutes, sprayed with the Gentamicin solution, and left to air-dry again for 15 minutes.

Identical treatment was applied to the other two titanium cylinders, of equal size, which were sprayed first with the HA-DOPA derivative solution and then with the Gentamicin solution, by the procedures described above.

Finally, two other titanium cylinders, of identical size, were sprayed with the PBS solution and then with the Gentamicin solution, by the procedures described above.

Each cylinder (total: 6) was then immersed once in MQ water for 5 seconds, left to air-dry for 15 minutes and inserted in a culture broth (Buffered Peptone Water: peptone 10.0 g/L, sodium chloride 5.0 g/L, anhydrous disodium phosphate 3.6 g/L, potassium phosphate 1.5 g/L, Biokar Diagnostics) inoculated with 600,000,000 CFU/mL of *Staphylococcus aureus*. The broth was incubated at 37° C., and at pre-set times (6 h, 12 h, 24 h, 48 h, 144 h) 1 mL of supernatant was taken up and diluted scalarly 1:10 (according to the bacterial growth), with sterile saline solution, for plate seeding (PCA—Plate Count Agar: tryptone 5.0 g/L, yeast extract 2.5 g/L, glucose 1.0 g/L, bacteriological agar 12.0 g/L. Manufactured by Biokar Diagnostics). The CFU/mL count was then conducted.

Figure 4:
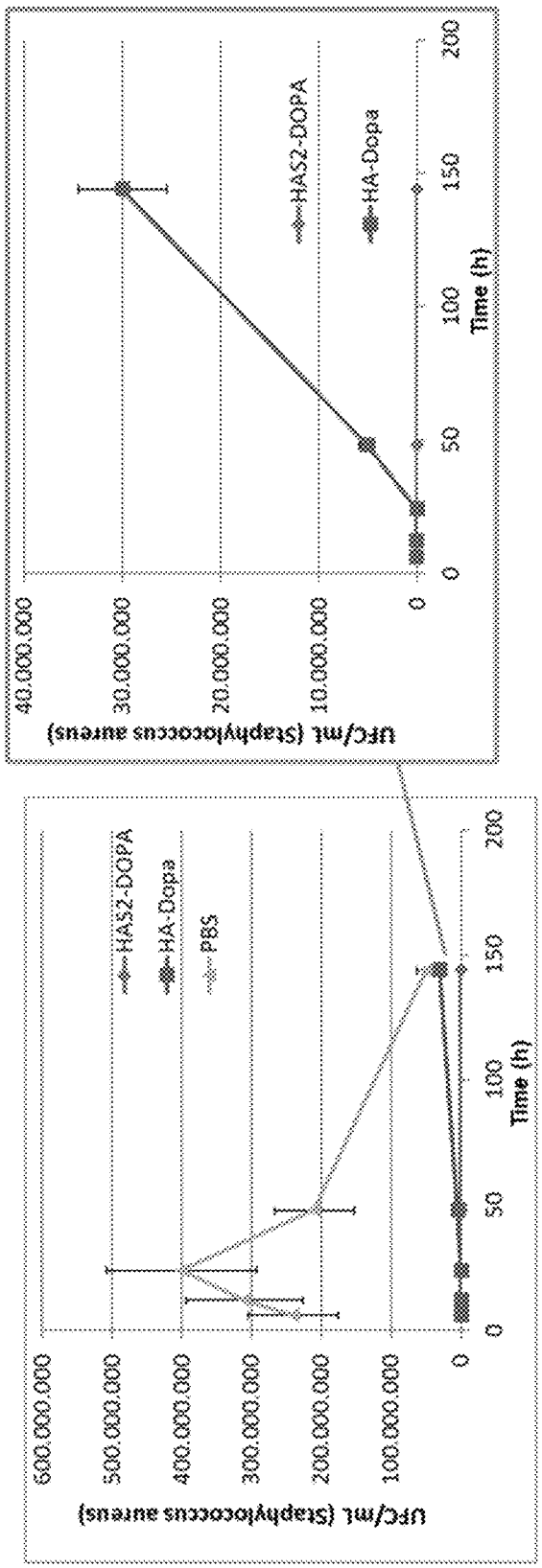
FIG. 4: Curves showing inhibition of growth of S. aureus on titanium cylinders functionalized with the HAS2-DOPA of example 3 or the HA-DOPA of example 12 coated with Gentamicin.

The percentage bacterial growth inhibition data over time compared with the initial inoculum of 600 million CFU/mL of *S. aureus* are set out in FIG. 4.

The graphs clearly show that:
HAS2-DOPA acts far more effectively than the control (PBS); this means that HAS2-DOPA releases Gentamicin in a controlled, constant way over time;
HAS2-DOPA acts in a much more significant way than HA-DOPA;
surprisingly, in addition to the total antimicrobial action in the first 24 hours, HAS2-DOPA maintains long-term antibacterial coverage for up to 144 hours, i.e. 7 days after inoculation, whereas HA-DOPA allows the proliferation of *S. aureus* to resume after only 48 hours.

A similar experiment was conducted with Daptomycin at the same concentrations, and an identical activity profile was obtained.

Example 15: Comparative Test: Antimicrobial Activity of HAS2-DOPA Conjugate Compared with Heparin-DOPA (HEPA-DOPA) Conjugate Bonded to Gentamicin The HAS2-DOPA conjugate was prepared as in Example 6, and the HEPA-DOPA derivative as in Example 11 (degree of derivatization: 21%).

Figure 5:
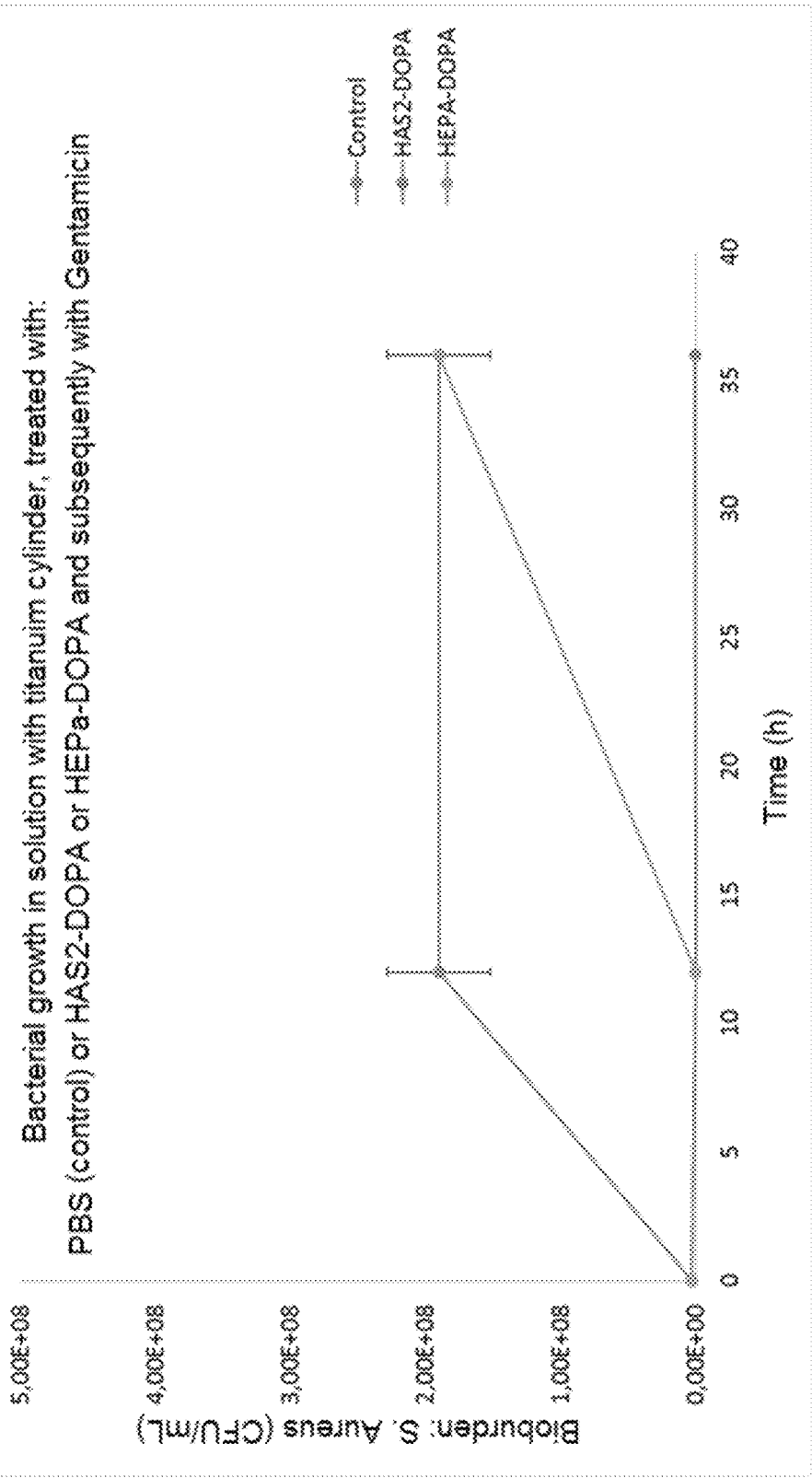
FIG. 5: Antimicrobial activity expressed in CFU/mL of the HAS2-DOPA conjugate of example 3 compared with the heparin-DOPA (HEPA-DOPA) conjugate of example 11 bonded to Gentamicin.

Two titanium cylinders (d=15×h=17 mm) were sprayed with HAS2-DOPA or HEPA-DOPA respectively, both at the concentration of 20 mg/mL in PBS at pH 8, and subsequently with Gentamicin at 5 mg/mL in MES, pH 5.2. 3 successive immersion washes (5 seconds) in MQ water were then performed; the purpose of the repeated washes is to eliminate all the Gentamicin not actually electrostatically bonded to the species tested. The cylinders were then inserted in the test tubes with an inoculum of *S. aureus* (600,000,000 CFU/mL); 1 mL of supernatant was taken up at preset times and then diluted scalarly 1:10 (according to the bacterial growth) with sterile saline solution for plate seeding (PCA—Plate Count Agar: tryptone 5.0 g/L, yeast extract 2.5 g/L, glucose 1.0 g/L, bacteriological agar 12.0 g/L (Biokar Diagnostics). The CFU/mL count was then conducted, as shown in FIG. 5.

The results demonstrate that the HAS2-DOPA product is far more active in inhibiting *S. aureus* proliferation, degree of derivatization and concentration being equal, and that said activity continues for at least 36 hours. This result is particularly significant in view of the fact that the HEPA-DOPA derivative progressively and rapidly loses its antibacterial activity, equalling the "Control" (which has no antibacterial activity) after 36 hours.

Example 16: Comparison of Anticoagulant Effect Between HAS2-DOPA and HEPA-DOPA

The HAS2-DOPA conjugate of Example 6 and the HEPA-DOPA derivative of Example 11 were prepared.

Figure 6:
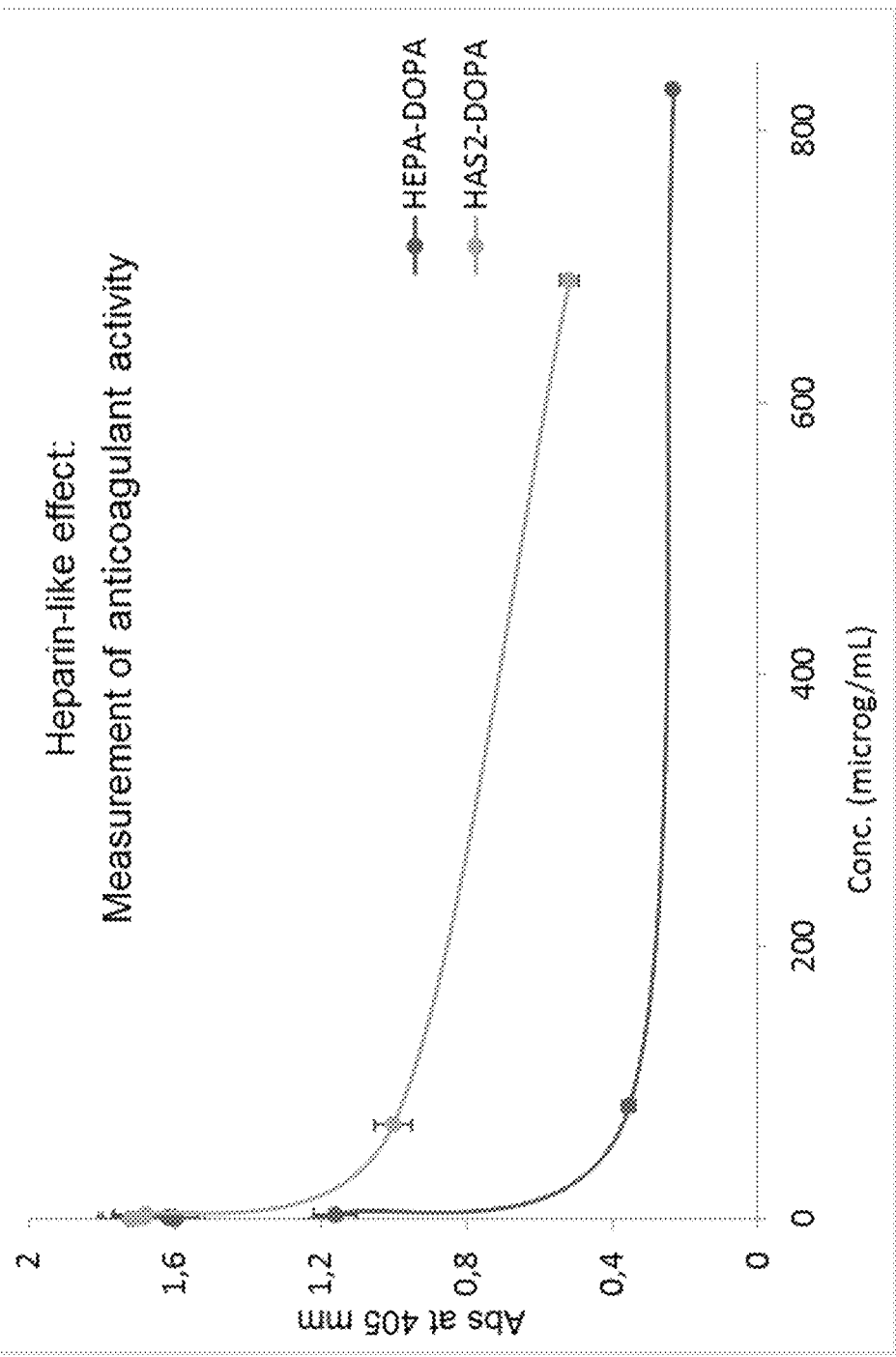
FIG. 6: Anticoagulant effect of the HAS2-DOPA of example 6 by comparison with the HEPA-DOPA of example 11.

The anticoagulant effect was evaluated using pure heparin as standard. A kit (Hyphen BioMed, Biophen Heparin AT+ Ref 221007) that employs a colorimetric method was used; the coagulation factor Xa not complexed and inhibited by the heparin or the test polymer is measured. The absorbance at 405 nm is directly proportional to the free Xa factor, and therefore inversely proportional to the heparin-like activity of the species tested (FIG. 6).

It is evident that the anticoagulant effect of HAS2-DOPA is far less than that of HEPA-DOPA, concentration being equal; in order to obtain the same effect (50% reduction in Abs) with the HAS2-DOPA system, a concentration about 50 times higher is needed. This means that the HAS2-DOPA conjugate performs a lower anticoagulant effect than known products, although it contains a sulphated polymer, exactly like heparin.

The HAS2-DOPA conjugate bonded to Gentamicin or to a similar antibacterial is advantageous because as well as being applicable by spraying, it can be used in very short times, has virtually no heparin-like effect and therefore does not produce abnormal bleeding, and acts in a far more effective, rapid, lasting way than the known equivalents.

Example 17: Evaluation of the Effect of HAS2-DOPA and HA-DOPA on Osteoblast Proliferation In Vitro The following were prepared:
an aqueous solution of HAS2-DOPA (23%, Example 3) 10 mg/mL
an aqueous solution of HA-DOPA (23%, Example 12) 10 mg/mL
an aqueous solution of fibronectin 20 µg/ml (positive control).

The circular upper surface of two 2 titanium cylinders (d=15×h=17 mm) was sprayed with the HAS2-DOPA solution and left to air-dry for 15 minutes; identical treatment was applied to the other two titanium cylinders, of equal size, which were sprayed with the HA-DOPA solution according to the procedures described above. Finally, two other titanium cylinders, of identical size, were sprayed with a solution of fibronectin in water, according to the procedures described above. Fibronectin is widely used as reference standard in cell proliferation experiments in vitro because it stimulates cell adhesion, proliferation and migration.

Each cylinder (total: 6) was then immersed once in MilliQ water for 5 seconds, left to air-dry for 15 minutes and inserted in a plate well; 0.10 mL of osteoblasts (Saos-2 cell line, from osteosarcoma) in culture medium (McCOY'S 5A+10% FBS), amounting to about 50000 cells/cm$^2$ of titanium, were then deposited on the surface of each cylinder. The cells were incubated on titanium for 4 h at 37° C. (5% $CO_2$) to allow adhesion; medium was then added until the cylinders were immersed, and incubation continued overnight under the same conditions.

The medium was eliminated the next day and the cylinders were washed with PBS to eliminate the non-adhering cells; an equal volume of the same medium was then added to each cylinder with 10% Alamar Blue, and the cylinders were left to incubate for 24 h at 37° C. (5% $CO_2$). After incubation the fluorescence reading was performed (A excitement: 530 nm and emission: 590 nm); the intensity of the fluorescence is proportional to the cell metabolism, and therefore to the number of viable osteoblasts.

Figure 7:
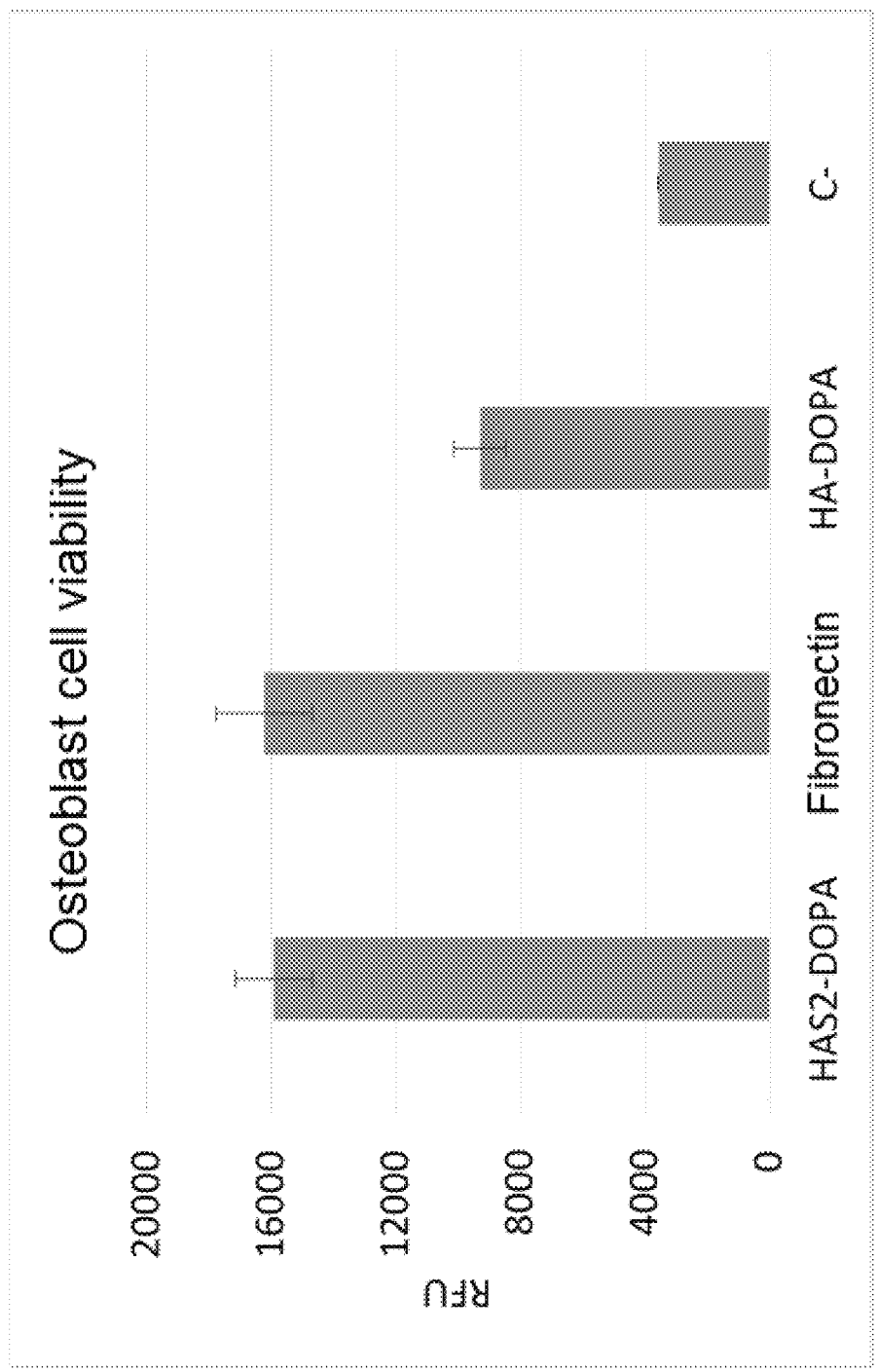
FIG. 7: Effect on osteoblast proliferation of the HAS2-DOPA of examples 3 and 12 by comparison with fibronectin.

The results (FIG. 7) demonstrate that, degree of derivatization and concentration being equal, HAS2-DOPA has a very high osteointegration activity, almost equal to that of fibronectin and, surprisingly, nearly twice that of HA-DOPA. The values are statistically significant.

C—represents the negative control, namely the titanium cylinder "as is", without seeding of osteoblasts.

Example 18: Evaluation of Stability to Beta- and Gamma-Ray Sterilization of 23% HAS2-DOPA Powder Prepared as in Example 3

As described in Example 3, three 1 g samples of 23% HAS2-DOPA powder were prepared. The samples were subjected, respectively, to:

sterilization with beta rays;
sterilization with gamma rays;
no sterilization (control).

The samples were then analysed by different known methods, namely structural analysis in $^1$H-NMR (Proton Nuclear Magnetic Resonance Spectroscopy) after dissolution of the powder in heavy water (D2O), with IR analysis (in KBr pellet) and finally, with visible UV analysis (UV-Vis) after dissolution in water.

The analysis results confirmed that the signals of the sterilized samples are identical, and above all that there is no difference between them and the signals of the unsterilized control. In particular, no signals due to the formation of by-products (NMR and IR analysis) or UV-Vis absorption signal shifts due, for example, to dopamine oxidation, were observed.

HAS2-DOPA polymer is therefore stable and compatible with beta- or gamma-ray sterilization.

Example 19: In Vitro Test of Inhibition of *S. aureus* Bacterial Growth on Titanium Cylinder Functionalized with HAS2-DOPA and Sterilized with Beta Rays and Subsequent Treatment with Vancomycin The following were prepared:
a solution of HAS2-DOPA (23%, Example 3), 10 mg/mL in water;
a solution of Vancomycin, 5 mg/ml in water.

One titanium cylinder (d=15×h=17 mm) (sample A, control) did not undergo any treatment, while a second titanium cylinder of the same dimensions (sample B) was sprayed with the HAS2-DOPA solution and left to air-dry for 15 minutes.

Both cylinders underwent sterilization by irradiation with beta rays, were subsequently sprayed with the prepared Vancomycin solution, and finally left to air-dry for 15 minutes.

Both cylinders were then immersed 10 times in different solutions of MQ water for 5 seconds, to eliminate the excess antibiotic present, and left to air-dry for 15 minutes. A suspension of *Staphylococcus aureus* (200 µL of O.D. at 650 nm>0.5) was evenly distributed on the surface of Mueller-Hinton agar (BD Biosciences) in a plate, and each of the two titanium cylinders was positioned in the center of the agar surface inoculated. The plate was incubated at 35° C. for 18 h, and the diameter of the surface on which bacterial growth was inhibited by the antibiotic was then measured.

Sample B, treated with HAS2-DOPA and sterilized, proved to inhibit bacterial growth far more effectively than the control sample, which was only sterilized.

This means that sterilization did not alter the structure or properties of HAS2-DOPA, which continues to remain anchored to the Ti and consequently retains its ability to bond to Vancomycin and subsequently release it.

A similar experiment was conducted with Gentamicin at the same concentrations and with Vancomycin on cross-linked titanium samples, under the same conditions and at the same concentrations, obtaining a bacterial growth inhibition profile identical to the one discussed above.

Beta-ray sterilization therefore:
does not alter the adhesion of HAS2-DOPA to titanium
does not alter the structural properties of HAS2-DOPA and therefore does not modify the ability of HAS2-DOPA to bond to an antibiotic and perform the desired antibacterial effect.

The invention claimed is:

1. A grade 2 sulphated hyaluronic acid having 2 to 60% molar of the carboxylic groups functionalized with dopamine conjugated either directly via an amide bond or via a spacer having an amino group for the formation of an amide bond with hyaluronic acid carboxylic groups and a carboxylic group for the formation of an amide bond with the dopamine amino group.

2. The sulphated hyaluronic acid according to claim 1, wherein dopamine is directly conjugated via an amide bond to 15-40%, of the sulphated hyaluronic acid carboxylic groups.

3. The sulphated hyaluronic acid according to claim 1, wherein dopamine is conjugated with sulphated hyaluronic acid via a spacer having an amino group for the formation of an amide bond with 2-20% of the sulphated hyaluronic acid carboxylic groups and a carboxyl group for the formation of an amide bond with the dopamine amino group.

4. The sulphated hyaluronic acid according to claim 3, wherein the spacer is a compound of formula HOOC—$(CH_2)_n$—$NH_2$ wherein n is an integer from 5 to 10.

5. The sulphated hyaluronic acid according to claim 3, wherein the spacer is a compound of formula HOOC—$(CH_2)_n$—O—$[(CH_2)_2$—O$]_m(CH_2)_2$—$NH_2$, wherein n is 1 or 2 and m is 1 or 2.

6. The sulphated hyaluronic acid according to claim 1 obtained by functionalisation of a grade 2 sulphated hyaluronic acid prepared from hyaluronic acid having a weight average molecular weight of 100,000 to 250,000 Da.

7. A salt of the sulphated hyaluronic acids of claim 1, further comprising one or more positively-charged medicaments.

8. The salt according to claim 7, wherein the positively-charged medicaments are selected from antibiotics, growth factors, and diclofenac in acid form.

9. The salt according to claim 8, wherein the positively-charged medicaments are selected from aminoglycoside antibiotics, Daptomycin, Ciprofloxacin, Meropenem, Vancomycin, Polymyxin, Colistin and Bacitracin.

10. The salt according to claim 9, wherein the aminoglycoside antibiotics are selected from Amikacin, Gentamicin and Tobramycin.

11. The salt according to claim 7, wherein the positively-charged medicaments are Gentamicin, Daptomycin, Polymyxin or Colistin.

12. A carrier for a medicament comprising the sulphated hyaluronic acids of claim 1.

13. A biomedical article comprising a coating of the sulphated hyaluronic acids of claim 1.

14. A titanium endoprostheses coated with one or more salts of claim 7.

15. The sulphated hyaluronic acid according to claim 2 obtained by functionalisation of a grade 2 sulphated hyaluronic acid prepared from hyaluronic acid having a weight average molecular weight of 100,000 to 250,000 Da.

16. The sulphated hyaluronic acid according to claim 3 obtained by functionalisation of a grade 2 sulphated hyaluronic acid prepared from hyaluronic acid having a weight average molecular weight of 100,000 to 250,000 Da.

17. The sulphated hyaluronic acid according to claim 4 obtained by functionalisation of a grade 2 sulphated hyaluronic acid prepared from hyaluronic acid having a weight average molecular weight of 100,000 to 250,000 Da.

18. The sulphated hyaluronic acid according to claim 5 obtained by functionalisation of a grade 2 sulphated hyaluronic acid prepared from hyaluronic acid having a weight average molecular weight of 100,000 to 250,000 Da.

19. A salt of the sulphated hyaluronic acids of claim 2 with positively-charged medicaments.

20. A salt of the sulphated hyaluronic acids of claim 3 with positively-charged medicaments.

\* \* \* \* \*